US012667313B2

(12) United States Patent
    García Saura et al.

(10) Patent No.: US 12,667,313 B2
(45) Date of Patent: Jun. 30, 2026

(54) NON-INVASIVE METHOD AND SYSTEM FOR CHARACTERISING AND CERTIFYING COGNITIVE ACTIVITIES

(71) Applicant: UNIVERSIDAD AUTÓNOMA DE MADRID, Madrid (ES)

(72) Inventors: Carlos García Saura, Madrid (ES); Irene Rodríguez Luján, Madrid (ES); Eduardo Serrano Jerez, Madrid (ES); Francisco De Borja Rodríguez Ortiz, Madrid (ES); Pablo Varona Martínez, Madrid (ES)

(73) Assignee: UNIVERSIDAD AUTÓNOMA DE MADRID, Madrid (ES)

( * ) Notice: Subject to any disclaimer, the term of this patent is extended or adjusted under 35 U.S.C. 154(b) by 794 days.

(21) Appl. No.: 17/757,954

(22) PCT Filed: Dec. 28, 2020

(86) PCT No.: PCT/ES2020/070822
    § 371 (c)(1),
    (2) Date: Aug. 12, 2022

(87) PCT Pub. No.: WO2021/130402
    PCT Pub. Date: Jul. 1, 2021

(65) Prior Publication Data
    US 2023/0022001 A1    Jan. 26, 2023

(30) Foreign Application Priority Data
    Dec. 27, 2019   (ES) ............................... ES201931165

(51) Int. Cl.
    *A61B 5/00*      (2006.01)
    *G01N 33/00*     (2006.01)
    *G16H 50/20*     (2018.01)

(52) U.S. Cl.
    CPC ............ *A61B 5/72* (2013.01); *G01N 33/0001* (2013.01); *G01N 33/0009* (2013.01); *G16H 50/20* (2018.01)

(58) Field of Classification Search
    CPC ......... A61B 5/72; A61B 5/165; A61B 5/7267; A61B 2010/0083; G01N 33/0001;
    (Continued)

(56) References Cited

U.S. PATENT DOCUMENTS

2019/0209022 A1 *  7/2019  Sobol ................. G08B 21/0272
    2021/0196168 A1    7/2021  Mitra

FOREIGN PATENT DOCUMENTS

DE    102008057086 A1 *  5/2010  ............. G08B 21/22
    EP    2946722 A1    11/2015

OTHER PUBLICATIONS

International Search Report in PCT/ES2020/070822, mailed Apr. 6, 2021, 4 pages.

(Continued)

*Primary Examiner* — Timothy P Graves
(74) *Attorney, Agent, or Firm* — McKee, Voorhees & Sease, PLC

(57)    ABSTRACT

The present invention relates to non-invasive method and system for characterising and certifying cognitive activities by detecting gaseous substances emitted by an organism, by means of the respiration, perspiration, and/or secretion, and changes measureable by sensors during said cognitive activities. Substance detection makes it possible to characterise the olfactory signal in order to determine and certify whether or not a cognitive activity has occurred and to classify said signals into different categories of cognitive activities.

21 Claims, 3 Drawing Sheets

(58) Field of Classification Search
      CPC .......................... G01N 33/0009; G16H 50/20;
                G06F 2218/00; G08B 21/0469; G08B
                                    21/0438
      See application file for complete search history.

(56)                     References Cited

OTHER PUBLICATIONS

Fonollosa et al., "Human activity monitoring using gas sensor arrays," Sensors and Actuators B: Chemical, 2014, vol. 199, pp. 398-402.
Kim et al., "ISSAQ: An Integrated Sensing Systems for Real-Time Indoor Air Quality Monitoring," IEEE Sensors Journal, 2014, vol. 14, No. 12, pp. 4230-4244.
Shaharil et al., "Classifying Sources Influencing Indoor Air Quality (IAQ) Using Artificial Neural Network (ANN)," Sensors, 2015, vol. 15, No. 5, pp. 11665-11684.

\* cited by examiner

NON-INVASIVE METHOD AND SYSTEM FOR CHARACTERISING AND CERTIFYING COGNITIVE ACTIVITIES

OBJECT OF THE INVENTION

The present invention relates to a non-invasive method and system for characterising and certifying cognitive activities.

BACKGROUND OF THE INVENTION

Cognitive activities are activities related to high-level mental processing which involve attention, concentration, learning, reasoning, and/or emotion. Cognitive processing typically involves little or no motor activity. Moreover, one and the same human activity may involve different cognitive activities. Many areas of human activity calls for the characterisation and certification of the performance of activities which require cognitive effort, such as work routines, user/customer/employee actions, examinations and/or tests, interviews, routines characterising a person's condition and/or health, etc.

Cognitive activities are typically characterised and certified through cognitive activity results reflected, for example, in a record/certificate indicating the actions performed, in a written text, or by means of an interview/gathering. The results are then analysed by mechanisms or entities which often invade the privacy of the monitored persons, for example, by means of monitoring with cameras, monitoring with microphones, monitoring with contact sensors, use of interactive programs, the presence of examiners, etc.

A cognitive activity is often monitored for the purpose of assessing the results of said cognitive activity, however, in many cases, there is a need to characterise the activity and certify its actual occurrence, its category, its time/duration, etc. This is a growing need in work, business, learning, and home environments, where the monitoring of routines and cognitive activities usually requires human interaction or privacy-invading methods. For example, in a scenario which requires home monitoring of the cognitive activities of a patient with a given disease, there is a need for invasive surveillance systems which compromise the patient's privacy, such as the case of surveillance cameras or microphones, as well as intervention by professionals capable of analysing the data of the surveillance systems in order to identify the cognitive activities of the patient and thereby detect possible abnormalities related to pathologies or to progression to the pathology, such as changes in daily cognitive routines, and also in sleep, hygiene, or nutrition.

DESCRIPTION OF THE INVENTION

The present invention proposes a solution to the preceding problems by means of a method for characterising and certifying cognitive activities, a system for characterising and certifying cognitive activities, a data processing system, a computer program, and a computer-readable medium.

A first inventive aspect provides a method for characterising and certifying cognitive activities by means of a characterisation and certification system comprising:

a detection module comprising at least one gaseous component measuring element configured for generating at least one signal indicating the temporal evolution of at least one detected gaseous component;

a characterisation module configured for characterising the at least one signal generated by the detection module based on the temporal evolution thereof and for determining whether said at least one signal corresponds to the development of a specific cognitive activity;

wherein the method comprises the following steps:

a) generating at least one signal indicating the temporal evolution of at least one gaseous component detected by means of the at least one measuring element of the detection module during a predetermined time period;

b) receiving the generated signal by means of the characterisation module;

c) characterising the signal based on the temporal evolution thereof by means of the characterisation module; and d) determining whether the signal corresponds to the development of a specific cognitive activity based on the result of the characterisation.

The method of the present invention provides a non-invasive mechanism for characterising and certifying cognitive activities by means of detecting and measuring the temporal evolution of gaseous components.

During the cognitive activity, the organism produces organic substances, hormones, and/or gases of varying composition (carbon dioxide, esters, acetone, urea, amines, alcohols, hydrogen, ammonia, methane, nitrogen monoxide, carbon monoxide, and other mixtures of organic compounds, such as VOCs (volatile organic compounds), which are released into the environment through processes such as respiration, perspiration, and secretion. The method and system of the present invention allow characterising the temporal evolution of these gaseous components and thereby determining whether a specific cognitive activity has been carried out.

In the context of the invention, characterising a cognitive activity should be understood as the identification of elements and patterns which allow describing specific properties of said activity by means of monitoring its evolution over time.

In the context of the invention, the occurrence of a specific cognitive activity is certified by verifying that its characteristic temporal evolution has taken place with the data obtained by means of the device.

Specific cognitive activity can be understood as belonging to a predefined category of cognitive activities. The examples of categories of cognitive activities are:

effective cognitive activity or cognitive activity that fulfils pre-established objectives; or cognitive activity associated with an emotion which causes the release of substances detectable by the system, preferably the emotion of pleasantness, satisfaction, relaxation, unpleasantness, dissatisfaction, or stress; or cognitive activity with a specific level of attention; or cognitive activity typical of a work routine; or cognitive activity typical of a school routine; or cognitive activity typical of a leisure routine; or cognitive activity typical of an examination or test; or cognitive activity typical of a job interview; or cognitive activity typical of a specific health condition of an individual; or a combination of any of the above.

The method and system of the present invention furthermore allow protecting the privacy of the monitored subjects because work is performed with environmental data which do not identify the persons. Advantageously, this non-invasive certification provides a technical solution to many applications such as routine monitoring in work, learning, home, and leisure contexts, cognitive process characterisation and certification (tasks, interviews, gatherings, assessment processes, etc.), and health condition monitoring by verifying the performance of cognitive routines.

Throughout the document, characterisation module should be understood as an array of media which are capable of processing, transmitting, and storing information; preferably, a computer comprising a processor, a communication device, and a memory. Characterising a signal should be understood as determining the attributes of the signal which make it unique, such that the signal can be clearly differentiated from other signals. Preferably, the signal is characterised based on its magnitude and sequential structure, individually or in combination with other signals, in the temporal evolution thereof, using parameters such as the amplitude of the signal, the maximums and minimums of the signal, the derivative value and/or the correlation of the signal with one or more additional signals.

Signal characterisation can be implemented with discrete-time variables (corresponding to specific characteristics and/or labels occurring at a given moment of the temporal evolution of the signals) and/or with continuous variables (the signal itself or those corresponding to operations the result of which is a continuous function that takes values during the acquisition process, such as the calculation of the signal derivative, the calculation of the signal integral, the combination of two or more signals, or the correlation of two or more signals). Label should be understood as a value assigned to the signal at a given moment in time in order to differentiate it from the other moments in time and/or to contextualise said value, where each label may originate from an automatic labelling process. One and the same label can be assigned to more than one signal at the same time in order to contextualise said signals.

In one embodiment, step d) of determining whether the signal corresponds to the development of a specific cognitive activity comprises performing a classification, a regression, or another process to associate the temporal structure of the measured signal with a specific cognitive activity.

In one embodiment, step (c) comprises identifying at least one temporal event in the signal and step (d) is performed based on the sequentiality of the identified temporal events.

In the context of the present invention, "temporal event" shall be understood as a particular incident characterising the signal which may correspond to a point or a more extensive region of the signal. Preferably, said temporal events are the presence of maximums or minimums, the values of slopes measured in the signal, the surpassing of predefined thresholds, and/or sequential sets of the foregoing which define a specific temporal structure. Each temporal event is identified based on the discrete and/or continuous variables characterising one or more signals.

Once the temporal events have been identified, whether the signals correspond to the development of a specific cognitive activity is determined based on the temporal structure of said temporal events. For example, a temporal structure of temporal events could be a sequence of local maximums, followed by the surpassing of a specific threshold. According to that example, if said sequence of temporal events occurs, the method determines that a specific cognitive activity has taken place.

The identification of temporal events and their sequentiality allow signals to be classified as a specific cognitive activity or as a family of cognitive activities (for example, gatherings of people, processes requiring study/concentration/attention/learning, processes involving learning assessment, i.e., examination, test, any attention and/or creative process, discussion, etc.), or as a cognitive activity with predefined characteristics (for example, a pleasurable activity).

In one embodiment, step (c) comprises using at least one algorithm for identifying temporal events and their temporality which uses, for example, the computation of signal derivatives, the detection of maximums/minimums, the detection of the surpassing of thresholds, and/or the correlation between signals. The signals are therefore characterised in relation to the sequentiality and temporality of the identified temporal events.

Signals shall be understood as those produced by the sensors and/or inputs of the system, including those which detect gaseous chemical substances originating from cognitive activity and another type of signals such as those relating to environmental conditions and/or external incidents.

In a particular example, the identification of temporal events in the signal further comprises a step of labelling said temporal events. Labelling should be understood as a process of assigning a temporal event with a distinctive label for said temporal event.

In a particular embodiment, if it is determined by means of the method that a cognitive activity has taken place, the method further comprises a step of classifying the signals into at least one subcategory of cognitive activity. In this embodiment, once it has been determined that a specific cognitive activity of a specific category has taken place, a more specific categorisation into subcategories of cognitive activities is performed. Some examples of specific cognitive activities and their possible subcategories are provided below:

Category: university class. Subcategories: mathematics, literature, etc.

Category: Examination. Subcategories: mathematics, economics, etc.

Category: pleasurable activity. Subcategories: very pleasurable, unpleasurable, etc.

Category: effective cognitive activity. Subcategories: studies, debate, essay, etc.

Category: health condition. Subcategories: good, poor, progressing positively, etc.

Category: Cognitive activity with a specific level of attention. Subcategories: great attention, little attention, undivided attention at a given moment.

During the course of cognitive activities, the measuring elements of the certification system generate signals associated with gaseous components. Different temporal events defining a characteristic temporal structure for each of said cognitive activities can be differentiated and quantified in said signals.

In a preferred embodiment, the system comprises an array of measuring elements configured for detecting a plurality of gaseous components.

In one embodiment, the gaseous component measuring element is an olfactory sensor. Preferably, the olfactory sensor is configured for detecting substances emitted by an organism by means of respiration, perspiration, and/or secretion. Preferably, the olfactory sensor is configured for detecting at least one of the following substances: carbon dioxide, esters, acetone, urea, amines, alcohols, hydrogen, ammonia, methane, nitrogen monoxide, carbon monoxide, and other mixtures of organic compounds, such as VOCs. In a more particular preferred embodiment, the system comprises a gaseous component measuring element which is configured for detecting carbon dioxide.

The addition of olfactory sensors in a device is usually called an "artificial nose" or an "electronic nose". Artificial noses are often applied in tasks involving threshold detection, odour differentiation/classification, warning systems, etc., and typically based on one-off measurements. In contrast, the present invention is based on the analysis of the temporal structure of the information recorded by the sensors during a prolonged measurement.

In one embodiment, the olfactory sensor is of any of the following types: chemoresistive, chemocapacitive, potentiometric, gravimetric, optical, acoustic, thermal, polymer, amperometric, chromatographic, spectrometric, or field effect sensor.

In one embodiment, the detection module further comprises at least one environmental condition detecting element for detecting environmental conditions, preferably humidity, temperature, atmospheric pressure, brightness, noise, and/or ventilation. In this embodiment, the method further comprises a step of obtaining measurements of at least one magnitude by means of the at least one environmental condition detecting element and of identifying temporal events of the signal which are associated with said at least one magnitude. Said identified temporal events are used as additional information during the step of characterising the signal.

In one embodiment, the detection module further comprises at least one external event recording element, preferably for recording the opening of doors and/or windows, for recording the activation or deactivation of a temperature control system, for recording the activation or deactivation of ventilation, and/or for recording times. In this embodiment, the method further comprises a step of identifying temporal events of the signal which are associated with the presence of external events. Said identified temporal events are used by means of the labelling thereof as additional information during the step of characterising the signal.

In a more particular preferred embodiment, the system comprises an external event recording element which is configured for recording the opening of doors and/or windows.

In a particular example, the identification of the temporal events associated with changes in the environmental conditions and/or with external events comprises a step of labelling said temporal events.

Advantageously, the detection of environmental conditions and/or the recording of external events provide additional information which allows contextualising the evolution of the recorded signal, as well as correlating temporal events detected in the signal with the information obtained about the environmental conditions and/or the occurrence of external events. This context information allows determining whether or not a specific cognitive activity has occurred with better results and/or obtaining a more precise signal classification.

In one embodiment, the system further comprises a conditioning module configured for conditioning the signal generated by the detection module. In this embodiment, the method further comprises, between steps (a) and (b), the steps of receiving and conditioning the signal by means of the conditioning module. In this embodiment, step (c) is performed on the generated and conditioned signal. In one embodiment, the step of conditioning the signal comprises filtering and/or sampling said signal.

In one embodiment, steps (c) and (d) are performed by means of a machine learning algorithm previously trained with training signals corresponding to at least one cognitive activity. In a preferred embodiment, in said training signals, a series of temporal events and of predefined labels are furthermore identified. When the method must classify the signal into different subcategories, the classification can also be performed by means of a machine learning algorithm previously trained with training signals which are classified into at least one predefined subcategory of cognitive activity.

In the embodiment in which steps (c) and (d) are performed by means of a machine learning algorithm, there is a prior training phase in which the signals obtained in the repeated recording of an activity which requires cognitive effort are used to train the machine learning algorithm, preserving the individual and combined temporal structure of the signals. In a preferred embodiment, the machine learning algorithm is supervised and comprises a neural network, and/or a random forest, and/or a support-vector machine with the coding and temporality requirements established by the type of classifier and by the characteristics of the signals produced by the device. The result of the training phase is an algorithm capable of extracting and comparing the temporal structure of events in the recorded signals with the representation thereof of a predefined activity.

Once constructed, the machine learning algorithm can be used for classifying the recorded signals according to their temporal structures in the so-called exploitation phase. The result of the exploitation phase is the determination of whether a signal corresponds to the development of a specific cognitive activity by classifying it as belonging to a specific category of cognitive activities. In all the processing steps, the temporal structure of both the individual signals and the integrated representation thereof is preserved, given that the sequentiality in the evolution of the temporal events is fundamental in order to characterise the cognitive activity. The temporality and/or sequentiality of temporal events in relation to the determination of the cognitive activity in general are not known a priori, and are represented in the machine learning algorithm with the information acquired during training.

In a particular example, there is an automatic labelling process for labelling all the types of temporal events (those corresponding to signals originating from the olfactory sensors, to changes in the environmental conditions, and/or to the presence of external events). The generated labels provide relevant information about the signal itself and about the context of its events in order to improve the results of the learning algorithms.

In a particular example, the results of the machine learning algorithm are also automatically labelled during the exploitation phase. As a result thereof, said automatic result labels are fed back to the machine learning algorithm itself so as to advantageously improve the precision of the algorithm in subsequent executions of the method.

In one embodiment, step (d) of the method comprises comparing the signal with at least one reference signal, preferably a reference signal encoded in the result of the learning algorithm used. For example, the representation of the reference signal in a trained neural network is reflected in the weights of the network connections. Additionally or alternatively, comparison with one or more reference signals can be used to classify the signal into at least one subcategory of cognitive activities.

In one embodiment, the steps of the method are repeated periodically, where the repetition period is a predefined value, in order to monitor the detected and/or classified cognitive activities. Advantageously, the method allows detecting changes in cognitive activities that should be repeated periodically.

In a particular example in the area of health, the method of the invention allows monitoring diseases which cause changes in a person's daily routines, such as neurodegenerative diseases. The method allows characterising daily routines related to cognitive activities of a healthy state (number of meals and schedules, hours of sleep, hours of leisure and physical exercise, etc.) and allows, by monitoring daily routines, detecting changes in said routines, possibly associated with the development of a specific pathology (an increase or decrease in the number of meals, deviations from usual schedules, etc.).

A second inventive aspect provides a system for characterising and certifying cognitive activities comprising:

a detection module comprising at least one gaseous component measuring element configured for generating at least one signal indicating the temporal evolution of at least one detected gaseous component;

a characterisation module configured for characterising the at least one signal generated by the detection module based on the temporal evolution thereof, for determining whether said at least one signal corresponds to the development of a specific cognitive activity;

and wherein the characterisation module is configured for carrying out steps (b) to (d) of the method according to any of the embodiments of the first inventive aspect.

Throughout the document, characterisation module should be understood as a set of media which are capable of processing, transmitting, and storing information; preferably a computer comprising a processor, a communication device, and a memory.

In one embodiment, the system further comprises a conditioning module configured for conditioning the signal generated by the detection module.

In one embodiment, the characterisation module of the system is further configured for classifying the at least one signal into at least one subcategory of cognitive activities.

In one embodiment, the system comprises:

at least one environmental condition detecting element for detecting environmental conditions, preferably humidity, temperature, atmospheric pressure, brightness, noise, and/or ventilation; and/or at least one external event recording element, preferably for recording the opening of doors and/or windows, for recording the activation or deactivation of a temperature control system, for recording the activation or deactivation of ventilation, and/or for recording times.

In a more particular preferred embodiment, the system comprises an external event recording element which is configured for recording the opening of doors and/or windows.

In one embodiment, the at least one gaseous component measuring element is an olfactory sensor. Preferably, the olfactory sensor is configured for detecting substances emitted by an organism by means of respiration, perspiration, and/or secretion.

Preferably, the olfactory sensor is configured for detecting at least one of the following substances: carbon dioxide, esters, acetone, urea, amines, alcohols, hydrogen, ammonia, methane, nitrogen monoxide, carbon monoxide, and other mixtures of organic compounds, such as VOCs.

In one embodiment, the olfactory sensor is of any of the following types: chemoresistive, chemocapacitive, potentiometric, gravimetric, optical, acoustic, thermal, polymer, amperometric, chromatographic, spectrometric, or field effect sensor.

In a preferred embodiment, the system comprises a plurality of non-invasive measuring elements configured for detecting a plurality of gaseous components. Preferably, the plurality of measuring elements is configured for detecting one or more of the following substances: carbon dioxide, esters, acetone, urea, amines, alcohols, hydrogen, ammonia, methane, nitrogen monoxide, carbon monoxide, and other mixtures of organic compounds, such as COVs. Preferably, the measuring elements are olfactory sensors.

In a more particular preferred embodiment, the system comprises a gaseous component measuring element which is configured for detecting carbon dioxide.

A third inventive aspect provides a data processing system comprising means for carrying out steps (b) to (d) of the method according to any of the embodiments of the first inventive aspect.

A fourth inventive aspect provides a computer program comprising instructions which, when the program is run by a computer, causes the computer to carry out steps (b) to (d) of the method according to any of the embodiments of the first inventive aspect.

A fifth inventive aspect provides a computer-readable medium comprising instructions which, when run by a computer, causes the computer to carry out steps (b) to (d) of the method according to any of the embodiments of the first inventive aspect.

All the features and/or the method steps described in this memory (including the claims, description, and drawings) can be combined in any combination, with the exception of the combinations of such mutually exclusive features.

DESCRIPTION OF THE FIGURES

These and other features and advantages of the invention will be more clearly understood based on the following detailed description of a preferred embodiment given only by way of non-limiting, illustrative example in reference to the attached figures.

DETAILED DESCRIPTION OF THE INVENTION

Figure 1:
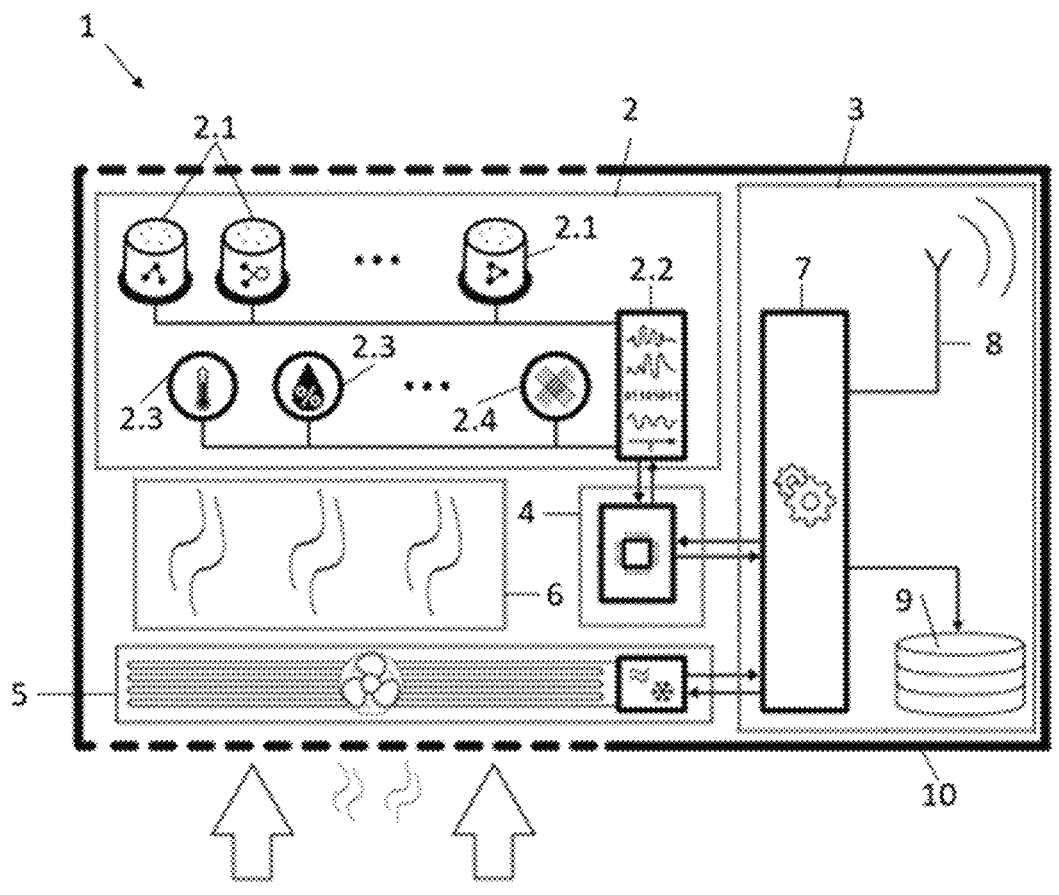
FIG. 1 This figure shows a schematic depiction of the system for characterising and certifying cognitive activities according to an embodiment of the invention.

The present invention proposes a method and system for characterising and certifying cognitive activities.

The system (1) for characterising and certifying cognitive activities comprises a detection module (2) and a characterisation module (3). The detection module (2) comprises at least one gaseous component measuring element (2.1). The measuring elements (2.1) detect gaseous substances produced by individuals through perspiration, respiration, and/or secretion processes and generate (110) signals (2.2) indicating the temporal evolution of the detected gaseous components. The characterisation module (3) receives (120) the signals (2.2) generated by the detection module (2), characterises (130) the signals (2.2) based on the temporal evolution thereof, and determines (141) whether a specific cognitive activity has occurred according to the characterisation.

In this embodiment, the characterisation module (3) is configured for determining (141) whether a specific cognitive activity has occurred by means of a classification method. In other embodiments, determination is carried out by means of a regression method or another method. As a result of the determination (141), the signals (2.2) are categorised into at least one category of cognitive activities.

If it is determined that a specific cognitive activity has occurred, said cognitive activity is certified (142) as being present, thereby verifying that it has taken place.

FIG. 1 shows a schematic depiction of the system (1) for characterising and certifying cognitive activities according to an embodiment of the invention. In this embodiment, the detection module (2) comprises a plurality of gaseous component measuring elements (2.1), environmental condition detecting elements (2.3), and external event recording elements (2.4). The gaseous component measuring elements (2.1) are olfactory sensors. In a preferred embodiment, the olfactory sensors are of a metal oxide (MOX) and non-dispersive infrared (NDIR) type and configured for recording substances such as carbon dioxide, esters, acetone, urea, amines, alcohols, hydrogen, ammonia, methane, nitrogen monoxide, carbon monoxide, and other mixtures of organic compounds, such as COVs. The environmental condition detecting elements (2.3) and the external event recording elements (2.4) provide data relating, respectively, to the environmental conditions and to the occurrence of external events during the course of the cognitive activity. This data allows contextualising the signals obtained by the olfactory sensors in order to determine whether or not a specific cognitive activity has occurred with better results.

In this embodiment, the environmental condition detecting elements (2.3) include temperature sensors, humidity sensors, atmospheric pressure sensors, brightness sensors, ventilation sensors, and environmental noise sensors, whereas the external event recording elements (2.4) include presence sensors (PIR), vibration sensors, and sensors for detecting the opening of windows/doors. The signals are contextualised based on data from these sensors, automatically generating labels which provide relevant information about the origin and context of the events; for example, a label informing of an increase in temperature or a label indicating the opening of a window.

In the embodiment of FIG. 1, the characterisation module (3) includes a processor (7), particularly a microcontroller, configured for receiving (120) the signals (2.2) generated by the detection module (2), for characterising (130) the signals (2.2) based on the temporal evolution thereof, and for determining (141) whether or not a specific cognitive activity has occurred based on the characterisation of the signals (2.2).

In one embodiment, the processor (7) is further configured for classifying the signals (2.2) into at least one subcategory of cognitive activities and/or for ordering the detection module (2) to generate the signals (2.2). If it is determined that the cognitive activity has occurred, said cognitive activity is certified (142) as being present, thereby verifying that it has taken place.

In the embodiment of FIG. 1, the characterisation module (3) further includes a wireless transmission system (8) and a memory (9). The wireless transmission system (8) allows data exchange with external processing and/or storage systems. In a preferred embodiment, the system is configured for transmitting data to a centralised server accessible through web and API REST, for storage. The memory (9) allows data to be stored in the system (1) itself.

API REST should be understood as a software architecture acting as a communication interface between two systems using HTTP.

The system (1) of FIG. 1 further includes a conditioning module (4) configured for conditioning the signal (2.2) generated by the detection module (2). In a preferred embodiment, the conditioning module (4) includes one or more operational amplifiers and one or more RLC filters.

In the embodiment shown in FIG. 1, the detection module (2) and the characterisation module (3) are implemented as parts of a single device and are housed inside a shell or casing (10) together with the rest of the elements of the system (1). However, in other embodiments, the detection module (2) and the characterisation module (3) can be implemented as separate devices.

The environmental condition detecting elements (2.3) and the external event recording elements (2.4) can:
  be integrated in the single device, or
  be independent peripheral elements which are connected to/disconnected from the system by means of a cable, and/or wirelessly, by means of technologies such as WiFi, Bluetooth, LoRA, Zigbee, or any type of mobile connectivity (3G, 4G, 5G, etc.).

The casing (10) has accesses whereby the entry and exit of air is allowed. In FIG. 1, these accesses have been depicted by means of discontinuous lines. In this embodiment, the system further includes an air capturing and conditioning system (5) which allows controlling and modifying variables such as temperature, humidity, and/or air flow entering the casing (10). In this embodiment, the system further includes an air diffusion system (6) for diffusing air towards the olfactory sensors (2.1), the environmental condition detecting elements (2.3), and/or the external event recording elements (2.4). Some of said sensors, such as the humidity and temperature sensors, require continuous access to external air to enable the performance of measurement. This access to external air is not needed for other sensors, such as some external event recording elements (2.4).

Figure 2:
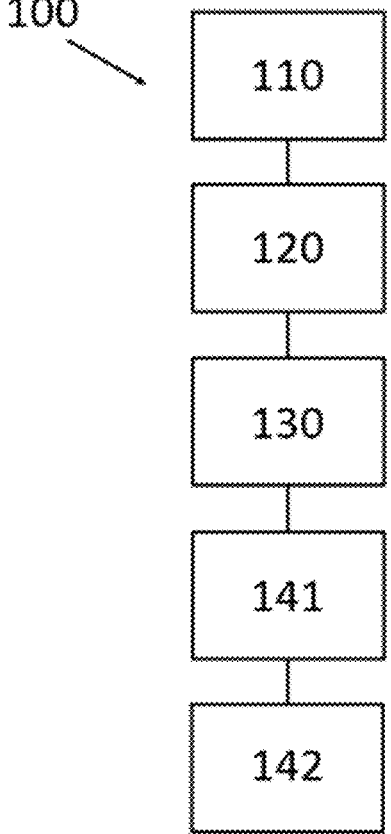
FIG. 2 This figure shows a schematic depiction of the method for characterising and certifying cognitive activities according to an embodiment of the invention.

FIG. 2 shows a schematic depiction of the method (100) for characterising and certifying cognitive activities according to an embodiment of the invention. This method (100) comprises the following steps:
  a) generating (110) at least one signal (2.2) indicating the temporal evolution of at least one gaseous component detected by means of the at least one measuring element (2.1) of the detection module (2) during a predetermined time period;
  b) receiving (120) the generated signal (2.2) by means of the characterisation module (3);
  c) characterising (130) the signal (2.2) based on the temporal evolution thereof by means of the characterisation module (3);
  d) determining (141) whether the signal (2.2) corresponds to the development of a specific cognitive activity based on the result of the characterisation;
  e) certifying (142) the occurrence of a specific cognitive activity if it is determined that the signal (2.2) corresponds with its characteristic temporal evolution.

Therefore, the method is based on recording the temporal evolution of the signals from the olfactory sensors (2.1) as described in relation to FIG. 1. If the system (1) includes environmental condition detecting elements (2.3) and/or external event recording elements (2.4), the additional data obtained from these sensors are optionally used, temporally synchronizing this additional data with the signals from the olfactory sensors (2.1). As described above, the additional data provided by the environmental condition detecting elements (2.3) and/or the external event recording elements (2.4) allows contextualising the evolution of the olfactory signals over the course of the cognitive activity such that more precise results are obtained in the determination of the occurrence of cognitive activities and/or in the classification of signals.

In this embodiment, the olfactory signal is labelled based on the detection of external events, such as the detection of the opening of a door or window or of the presence of devices and network traffic by means of Bluetooth, WiFi, or other technologies which allow estimating the occupation of the environment and knowing whether the devices are being used for a cognitive activity, for example, a leisure activity. Furthermore, additionally or alternatively, the olfactory signal can be labelled based on a detected environmental condition, such as an increase in temperature or pressure.

The characterisation module (3) receives (120) the generated signal (2.2), characterises (130) it based on the temporal evolution thereof, determines (141) whether said signal (2.2) corresponds with a specific cognitive activity by means of classifying same, and in this case, certifies (142) the activity as being present. Additionally, in one embodiment, said module reclassifies the cognitive activity into at least one predefined subcategory of cognitive activities. In a preferred embodiment, the olfactory signals are first time-synchronised and re-sampled, being adapted to the original temporisation and to the type of data obtained (continuous/discrete measurements, labels, etc.). Algorithms are then used for identifying temporal events in the structure of the signals and the temporality and/or sequentiality of said temporal events, for example, by means of the computation of the signal derivative, the detection of maximums and/or minimums in the signal, the surpassing of predefined thresholds by the signal, the correlation between signals, etc.

In a preferred embodiment, the characterisation (130) of the signal (2.2), the determination (141) of whether the signal (2.2) corresponds to the development of a cognitive activity, and the classification of said signal (2.2) are performed by means of a previously trained machine learning algorithm. In the prior training phase, training signals (3.3) classified into predefined categories of cognitive activity, as well as additional data and labels obtained during the repeated recording of said predefined cognitive activity are fed to the machine learning algorithm. The machine learning algorithm is thereby trained, preserving the individual and combined temporal structure of the information obtained from the sensors and their labels. In a preferred embodiment, the machine learning algorithm is supervised and is based on a neural network, and/or a random forest, and/or support-vector machine with the established coding and temporality requirements. The result of the training is an algorithm which is capable of extracting (131) the temporal structure of events in the recorded olfactory signals (2.2) and comparing it with its representation of predefined cognitive activities.

Once the machine learning algorithm has been trained, upon providing a recorded olfactory signal (2.2) and optionally additional data thereto, the machine learning algorithm is capable of determining (141) whether a signal corresponds to the development of a specific cognitive activity by means of classifying same (i.e., classifying that the activity belongs to a specific category of cognitive activities or identifying that the activity does not correspond to any of said predefined cognitive activities). Additionally, training can be improved by feeding the generated automatic result labels of said algorithm back to the machine learning algorithm.

In one embodiment, data acquisition is performed throughout the day and the steps of the method are repeated daily for the purpose of monitoring the detected and/or classified cognitive activities.

In a particular example, the method outlined in FIG. 2 is used for monitoring the health condition of a patient diagnosed with early Alzheimer. In this case, the device in charge of carrying out the monitoring is preferably installed in different rooms (bedroom, kitchen, living room, bathroom) of the patient's house and connected to the house's WiFi network. The information is centralised in a server configured for processing the data it receives. Classification of cognitive activities is performed by means of a machine learning algorithm which requires a first training phase. In said first training phase, the acquired olfactory signals (2.2) resulting from the patient's daily activity are characterised, labelling the different events of his/her daily life which are related with one or more types of cognitive activities (periods of sleep, periods of being awake, meal schedule, leisure, use of electronic devices, interaction with other people, use of bathroom, etc). Once the machine learning algorithm is trained, the device characterises the olfactory signals (2.2) resulting from the patient's cognitive activities in the subsequent days, for example, with a daily periodicity, to enable monitoring changes in the patient's routines. For example, the delay or absence of one or more events (for example, meals), sleep disorders, changes in usual leisure routines, etc. These changes in the routines characteristic of the pathology would finally be certified by means of the method and, if problems are detected, health services would be informed so that they may activate the appropriate protocols.

Figure 3:
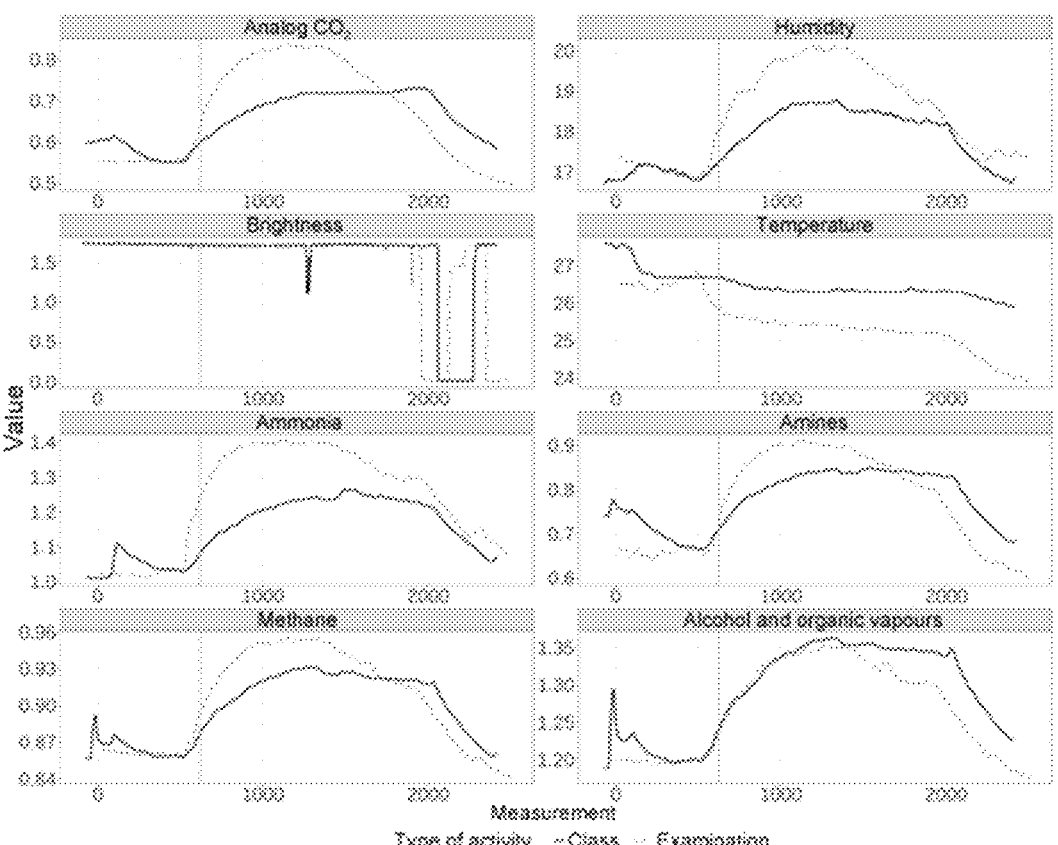
FIG. 3 This figure shows an example of the signals collected over the course of a cognitive activity in a university class in two different conditions.

FIG. 3 shows an example of the signals collected by the sensors over the course of two cognitive activities developed in a university class. The temporal series shown correspond to two classroom activities: an examination (discontinuous line) and a slide presentation (continuous line) in the same group of people. Dates close to each other and the same time have been considered in order to reduce any type of bias relating to external environmental conditions. In particular, the series correspond to:

Activity 1: Class with projected presentation (activity with moderate cognitive attention).

Activity 2: Examination taken by the same subject (activity with intense cognitive attention).

The panels of FIG. 3 show the evolution of the signals recorded by 8 sensors of the device, respectively:

5 olfactory sensors, configured for detecting $CO_2$, ammonia, amines, methane, and a mixture of alcohols/esters/acetone and other organic substance, and 3 environmental condition sensors configured for detecting humidity, brightness, and temperature.

The signals correspond to samplings every 5 seconds and were acquired by the device of the preferred embodiment from one hour before the start of the cognitive activity up to two and a half hours after the start. The start of the cognitive activity (start of the class and examination) is illustrated in the graphs with a vertical line. The temporal series of all the sensors have been aligned such that the start of the two activities is the same. The value of the signals recorded by the sensors increases before the start of the cognitive activity due to the gradual occupation of the classroom.

The different temporal evolution of the signals measured by the sensors in the two types of cognitive activity can be seen in the panels. Significant differences in the temporal evolution of the signals (in terms of slope, maximum and minimum levels, and characteristics of the temporal structure) of all the olfactory sensors can be seen, with the sensor recording the mixture of alcohols/esters/acetone being the less discriminative in this example. The other environmental (humidity, temperature, and brightness) sensors provide additional information which allows contextualising the temporal evolution of the signals from the olfactory sensors. In one embodiment, this contextualisation is performed by detecting the events of change in brightness, temperature, and/or humidity in order to generate relevant labels for the characterisation module (3). For example, in the panel showing the evolution of brightness, a sudden decrease associated with the light being switched off is observed. In this example, the method would generate a "light off" label to contextualise the information provided by the rest of the sensors (start/end of the activity).

CLAUSES

The first clause provides a method (100) for characterising and certifying cognitive activities by means of a characterisation and certification system (1), comprising:

a detection module (2) comprising at least one gaseous component measuring element (2.1) configured for generating at least one signal (2.2) indicating the temporal evolution of at least one detected gaseous component;

a characterisation module (3) configured for characterising the at least one signal (2.2) generated by the detection module (2) based on the temporal evolution thereof and for determining whether said at least one signal (2.2) corresponds to the development of a specific cognitive activity;

wherein the method (100) comprises the following steps:

a) generating (110) at least one signal (2.2) indicating the temporal evolution of at least one gaseous component detected by means of the at least one measuring element (2.1) of the detection module (2) during a predetermined time period;

b) receiving (120) the generated signal (2.2) by means of the characterisation module (3);

c) characterising (130) the signal (2.2) based on the temporal evolution thereof, by means of the characterisation module (3); and d) determining (141) whether the signal (2.2) corresponds to the development of a specific cognitive activity based on the result of the characterisation.

2. The method (100) according to the preceding clause, wherein the system (1) comprises a conditioning module (4) configured for conditioning the signal (2.2) generated by the detection module (2); and wherein the method (100) further comprises, between steps (a) and (b), the steps of receiving and conditioning the signal (2.2) by means of the conditioning module (4), and wherein step (c) is performed on the generated and conditioned signal.

3. The method (100) according to the preceding clause, wherein the step of conditioning the signal (2.2) comprises filtering and/or sampling said signal (2.2).

4. The method (100) according to any of the preceding clauses, wherein steps (c) and (d) are performed by means of a machine learning algorithm previously trained with training signals (3.3) corresponding to at least one cognitive activity.

5. The method (100) according to any of the preceding clauses, wherein the cognitive activity belongs to one of the following categories:— effective cognitive activity or cognitive activity that fulfils pre-established objectives; or cognitive activity associated with an emotion which causes the release of substances detectable by the device, preferably the emotion of pleasantness, satisfaction, relaxation, unpleasantness, dissatisfaction, or stress; or cognitive activity with a specific level of attention; or cognitive activity typical of a work routine; or cognitive activity typical of a school routine; or cognitive activity typical of a leisure routine; or cognitive activity typical of an examination or test; or cognitive activity typical of a job interview; or cognitive activity typical of a specific health condition of an individual; or a combination of any of the above.

6. The method (100) according to any of the preceding clauses, wherein the method further comprises classifying the at least one signal (2.2) into at least one subcategory of cognitive activities by means of the characterisation module (3).

7. The method (100) according to clause 6, wherein the classification of the signal (2.2) is performed by means of a machine learning algorithm previously trained with training signals (3.3) which are classified into at least one predefined subcategory of cognitive activity.

8. The method (100) according to any of the preceding clauses, wherein step (c) comprises identifying (131) at least one temporal event (3.2) in the signal (2.2), and wherein the determination of step (d) is performed based on the sequentiality of the identified temporal events (3.2).

9. The method (100) according to clauses 6 and 8, wherein classification of the signal (2.2) is performed based on the sequentiality of the identified temporal events (3.2).

10. The method (100) according to any of clauses 8 to 9, wherein the temporal events (3.2) detected in the signal (2.2) comprise maximums, minimums, slopes, the surpassing of thresholds, and/or sequential sets of the foregoing which define a specific temporal structure.

11. The method (100) according to any of the preceding clauses, wherein the at least one gaseous component measuring element (2.1) is an olfactory sensor, said olfactory sensor preferably being configured for detecting at least one substance emitted by an organism during a cognitive activity; the substance preferably being at least one of: carbon dioxide, esters, acetone, urea, amines, alcohols, hydrogen, ammonia, methane, nitrogen monoxide, carbon monoxide, and other mixtures of organic compounds, such as VOCs (volatile organic compounds).

12. The method (100) according to clause 11, wherein the olfactory sensor is of any of the following types: chemoresistive, chemocapacitive, potentiometric, gravimetric, optical, acoustic, thermal, polymer, amperometric, chromatographic, spectrometric, or field effect sensor.

13. The method (100) according to any of the preceding clauses, wherein:

the detection module (2) further comprises at least one detection element (2.3) for detecting environmental conditions, preferably humidity, temperature, atmospheric pressure, brightness, noise, and/or ventilation;

the method (100) further comprises a step of obtaining measurements of at least one magnitude by means of the at least one environmental condition detecting element (2.3) and of identifying temporal events (3.2) of the signal (2.2) which are associated with said at least one magnitude;

and wherein said identified temporal events (3.2) are used as additional information during the step of characterising (130) the signal (2.2).

14. The method (100) according to any of the preceding clauses, wherein:— the detection module (2) further comprises at least one external event recording element (2.4), preferably for recording the opening of doors or windows, for recording the activation or deactivation of a temperature control system, for recording the activation or deactivation of ventilation, and/or for recording times;

the method (100) further comprises a step of identifying temporal events (3.2) of the signal (2.2) which are associated with the presence of external events;

and wherein said identified temporal events (3.2) are used as information additional during the step of characterising (130) the signal (2.2).

15. The method (100) according to any of the preceding clauses, wherein step (c) of the method (100) comprises comparing the signal (2.2) with at least one reference signal.

16. The method (100) according to any of the preceding clauses, wherein the steps of the method are repeated periodically, where the repetition period is a predefined value, in order to monitor the detected and/or classified cognitive activities.

17. A system (1) for characterising and certifying cognitive activities, comprising:

a detection module (2) comprising at least one gaseous component measuring element (2.1) configured for generating at least one signal (2.2) indicating the temporal evolution of at least one detected gaseous component;

a characterisation module (3) configured for characterising the at least one signal (2.2) generated by the detection module (2) based on the temporal evolution thereof, for determining whether said at least one signal (2.2) corresponds to the development of a specific cognitive activity;

wherein the characterisation module (3) is configured for carrying out steps (b) to (d) of the method according to any of the preceding clauses.

18. The system (1) according to clause 17, further comprising a conditioning module (4) configured for conditioning the signal (2.2) generated by the detection module (2).

19. The system (1) according to any of clauses 17 or 18, wherein the characterisation module (3) of the system (1) is further configured for classifying the at least one signal (2.2) into at least one subcategory of cognitive activities.

20. The system (1) according to any of clauses 17 to 19, comprising:

at least one environmental condition detecting element (2.3) for detecting environmental conditions, preferably humidity, temperature, atmospheric pressure, brightness, noise, and/or ventilation; and/or at least one external event recording element (2.4), preferably for recording the opening of doors or windows, for recording the activation or deactivation of a temperature control system, for recording the activation or deactivation of ventilation, and/or for recording times.

21. The system (1) according to any of clauses 17 to 20, wherein the at least one gaseous component measuring element (2.1) is an olfactory sensor, said olfactory sensor preferably being configured for detecting at least one substance emitted by an organism during a cognitive activity; the substance preferably being at least one of: carbon dioxide, esters, acetone, urea, amines, alcohols, hydrogen, ammonia, methane, nitrogen monoxide, carbon monoxide, and other mixtures of organic compounds, such as VOCs (volatile organic compounds).

22. The system (1) according to clause 21, wherein the olfactory sensor is of any of the following types: chemoresistive, chemocapacitive, potentiometric, gravimetric, optical, acoustic, thermal, polymer, amperometric, chromatographic, spectrometric, or field effect sensor.

23. A data processing system comprising means for carrying out steps (b) to (d) of the method (100) according to any of clauses 1 to 16.

24. A computer program comprising instructions which, when the program is run by a computer, causes the computer to carry out steps (b) to (d) of the method (100) according to any of clauses 1 to 16.

25. A computer-readable medium comprising instructions which, when run by a computer, causes the computer to carry out steps (b) to (d) of the method (100) according to any of clauses 1 to 16.

The invention claimed is:

1. A method for characterising and certifying cognitive activities in a non-invasive manner by means of a characterisation and certification system, comprising:

a detection module comprising at least one gaseous component measuring element configured for generating at least one signal indicating a temporal evolution of at least one detected gaseous component;

a characterisation module configured for characterising the at least one signal generated by the detection module based on an individual or combined sequential structure of the temporal evolution thereof and for determining whether said at least one signal corresponds to a development of a specific cognitive activity; and a machine learning algorithm that is trained with a method comprising acquiring the at least one detected gaseous component over time in the form of the at least one signal and classifying known activities associated with the acquired at least one signal as a result label, wherein the known activities are associated with one or more cognitive activities;

wherein the method comprises the following steps:

a) generating at least one signal indicating the temporal evolution of at least one gaseous component corresponding to the specific cognitive activity detected by means of the at least one measuring element of the detection module during a predetermined time period;

b) receiving the generated signal by means of the characterisation module;

c) characterising the generated signal based on the sequential structure of events in the temporal evolution thereof, by means of the characterisation module; and d) determining whether the generated signal corresponds to the development of the specific cognitive activity based on a result of the characterisation;

wherein step (c) comprises identifying at least one temporal event in the signal, and wherein the determination of step (d) is performed based on the sequentiality of the identified temporal events; and wherein steps (c) and (d) are performed using the trained machine learning algorithm, which uses the sequential structure of the temporal evolution of the cognitive activity;

wherein the method further comprises classifying the at least one signal into at least one subcategory of cognitive activities by means of the characterisation module; and wherein the classification of the signal is performed by means of the machine learning algorithm previously trained with training signals which are classified into at least one predefined subcategory of cognitive activity, and wherein the result label is fed back into the machine learning algorithm to improve precision thereof.

2. The method according to claim 1, wherein the system comprises a conditioning module configured for conditioning the signal generated by the detection module; and wherein the method further comprises, between steps (a) and (b), the steps of receiving and conditioning the generated signal by means of the conditioning module, and wherein step (c) is performed on the generated and conditioned signal.

3. The method according to claim 2, wherein the step of conditioning the generated signal comprises filtering and/or sampling said generated signal maintaining the sequential structure of the temporal evolution of the cognitive activity.

4. The method according to claim 1, wherein the cognitive activity belongs to one of the following categories:

effective cognitive activity or cognitive activity that fulfils pre-established objectives; or cognitive activity associated with an emotion which causes the release of substances detectable by the device; or cognitive activity with a specific level of attention; or cognitive activity typical of a work routine; or cognitive activity typical of a school routine; or cognitive activity typical of a leisure routine; or cognitive activity typical of an examination or test; or cognitive activity typical of a job interview; or cognitive activity typical of a specific health condition of an individual; or a combination of any of the above.

5. The method according to claim 1, wherein classification of the signal is performed based on the sequentiality of the identified temporal events.

6. The method according to claim 1, wherein the temporal events detected in the signal comprise maximums, minimums, slopes, the surpassing of thresholds, and/or sequential sets of the foregoing which define a specific temporal structure.

7. The method according to claim 1, wherein the at least one gaseous component measuring element is an olfactory sensor, said olfactory sensor being configured for detecting at least one substance emitted by an organism during a cognitive activity.

8. The method according to claim 7, wherein the olfactory sensor is of any of the following types: chemoresistive, chemocapacitive, potentiometric, gravimetric, optical, acoustic, thermal, polymer, amperometric, chromatographic, spectrometric, or field effect sensor.

9. The method according to claim 1, wherein:

the detection module further comprises at least one environmental condition detecting element for detecting environmental conditions;

the method further comprises a step of obtaining measurements of at least one magnitude by means of the at least one environmental condition detecting element and of identifying temporal events of the signal which are associated with said at least one magnitude; and wherein said identified temporal events are used as additional context information during the step of characterising the signal.

10. The method according to claim 1, wherein:

the detection module further comprises at least one external event recording element;

the method further comprises a step of identifying temporal events of the signal which are associated with the presence of external events; and wherein said identified temporal events are used as additional context information during the step of characterising the signal.

11. The method according to claim 1, wherein step (c) of the method comprises comparing the generated signal with at least one reference signal of the cognitive activity.

12. The method according to claim 1, wherein the steps of the method are repeated periodically, where the repetition period is a predefined value, in order to monitor the detected and/or classified cognitive activities.

13. A non-invasive system for characterising and certifying cognitive activities, comprising:

a detection module comprising at least one gaseous component measuring element configured for generating at least one signal indicating a temporal evolution of at least one detected gaseous component;

a characterisation module configured for characterising the at least one signal generated by the detection module based on an individual or combined sequential structure of the temporal evolution thereof, for determining whether said at least one signal corresponds to a development of a specific cognitive activity;

a machine learning algorithm that is trained with a method comprising acquiring the at least one detected gaseous component over time in the form of the at least one signal and classifying known activities associated with the acquired at least one signal as a result label, wherein the known activities are associated with one or more cognitive activities;

wherein the characterisation module is configured to:

a) receive the generated signal by means of the characterisation module;

b) characterise the generated signal based on the sequential structure of events in the temporal evolution thereof, by means of the characterisation module; and c) determine whether the generated signal corresponds to the development of a specific cognitive activity based on the result of the characterisation;

wherein step (b) comprises identifying at least one temporal event in the generated signal, and wherein the determination of step (c) is performed based on the sequentiality of the identified temporal events; and wherein steps (b) and (c) are performed using the trained machine learning algorithm, which uses the sequential structure of the temporal evolution of the cognitive activity;

wherein the method further comprises classifying the at least one signal into at least one subcategory of cognitive activities by means of the characterisation module; and wherein the classification of the signal is performed by means of the machine learning algorithm previously trained with training signals which are classified into at least one predefined subcategory of cognitive activity, and wherein the result label is fed back into the machine learning algorithm to improve precision thereof.

14. The system according to claim 13, further comprising a conditioning module configured for conditioning the signal originating from a specific cognitive activity generated by the detection module.

15. The system according to claim 13, wherein the characterisation module of the system is further configured for classifying the at least one signal into at least one subcategory of cognitive activities.

16. The system according to claim 13, comprising contextualization elements of cognitive activity:

at least one environmental condition detecting element for detecting environmental conditions; and/or at least one external event recording element.

17. The system according to claim 13, wherein the at least one gaseous component measuring element is an olfactory sensor, said olfactory sensor being configured for detecting at least one substance emitted by an organism during a cognitive activity.

18. The system according to claim 17, wherein the olfactory sensor is of any of the following types: chemoresistive, chemocapacitive, potentiometric, gravimetric, optical, acoustic, thermal, polymer, amperometric, chromatographic, spectrometric, or field effect sensor.

19. A system for characterising and certifying cognitive activities in a non-invasive manner by means of a characterisation and certification system, comprising:

a detection module comprising at least one gaseous component measuring element configured for generating at least one signal indicating a temporal evolution of at least one detected gaseous component;

a characterisation module configured for characterising the at least one signal generated by the detection module based on an individual or combined sequential structure of the temporal evolution thereof and for determining whether said at least one signal corresponds to a development of a specific cognitive activity; and a machine learning algorithm that is trained with a method comprising acquiring the at least one detected gaseous component over time in the form of the at least one signal and classifying known activities associated with the acquired at least one signal as a result label, wherein the known activities are associated with one or more cognitive activities;

a data processing system comprising means to:

a) receive the generated signal by means of the characterisation module;

b) characterise the generated signal based on the sequential structure of events in the temporal evolution thereof, by means of the characterisation module; and c) determine whether the generated signal corresponds to the development of a specific cognitive activity based on the result of the characterisation;

wherein step (b) comprises identifying at least one temporal event in the generated signal, and wherein the determination of step (c) is performed based on the sequentiality of the identified temporal events; and wherein steps (b) and (c) are performed using the trained machine learning algorithm, which uses the sequential structure of the temporal evolution of the cognitive activity;

wherein the method further comprises classifying the at least one signal into at least one subcategory of cognitive activities by means of the characterisation module; and wherein the classification of the signal is performed by means of the machine learning algorithm previously trained with training signals which are classified into at least one predefined subcategory of cognitive activity, and wherein the result label is fed back into the machine learning algorithm to improve precision thereof.

20. A system for characterising and certifying cognitive activities in a non-invasive manner by means of a characterisation and certification system, comprising:

a detection module comprising at least one gaseous component measuring element configured for generating at least one signal indicating a temporal evolution of at least one detected gaseous component;

a characterisation module configured for characterising the at least one signal generated by the detection module based on an individual or combined sequential structure of the temporal evolution thereof and for determining whether said at least one signal corresponds to a development of a specific cognitive activity; and a machine learning algorithm that is trained with a method comprising acquiring the at least one detected gaseous component over time in the form of the at least one signal and classifying known activities associated with the acquired at least one signal as a result label, wherein the known activities are associated with one or more cognitive activities;

a tangible, non-transitory computer readable medium storing a computer program comprising instructions which, when the program is run by a computer, causes the computer to:

a) receive the generated signal by means of the characterisation module;

b) characterise the generated signal based on the sequential structure of events in the temporal evolution thereof, by means of the characterisation module; and c) determine whether the generated signal corresponds to the development of a specific cognitive activity based on the result of the characterisation;

wherein step (b) comprises identifying at least one temporal event in the signal, and wherein the determination of step (c) is performed based on the sequentiality of the identified temporal events; and wherein steps (b) and (c) are performed using the trained machine learning algorithm, which uses the sequential structure of the temporal evolution of the cognitive activity;

wherein the method further comprises classifying the at least one signal into at least one subcategory of cognitive activities by means of the characterisation module; and wherein the classification of the signal is performed by means of the machine learning algorithm previously trained with training signals which are classified into at least one predefined subcategory of cognitive activity, and wherein the result label is fed back into the machine learning algorithm to improve precision thereof.

21. A system for characterising and certifying cognitive activities in a non-invasive manner by means of a characterisation and certification system, comprising:

a detection module comprising at least one gaseous component measuring element configured for generating at least one signal indicating a temporal evolution of at least one detected gaseous component;

a characterisation module configured for characterising the at least one signal generated by the detection module based on an individual or combined sequential structure of the temporal evolution thereof and for determining whether said at least one signal corresponds to a development of a specific cognitive activity; and a machine learning algorithm that is trained with a method comprising acquiring the at least one detected gaseous component over time in the form of the at least one signal and classifying known activities associated with the acquired at least one signal as a result label, wherein the known activities are associated with one or more cognitive activities;

a tangible, non-transitory computer-readable medium comprising instructions which, when run by a computer, causes the computer to:

a) receive the generated signal by means of the characterisation module;

b) characterise the generated signal based on the sequential structure of events in the temporal evolution thereof, by means of the characterisation module; and c) determine whether the generated signal corresponds to the development of a specific cognitive activity based on the result of the characterisation;

wherein step (b) comprises identifying at least one temporal event in the signal, and wherein the determination of step (c) is performed based on the sequentiality of the identified temporal events; and wherein steps (b) and (c) are performed using the trained machine learning algorithm, which uses the sequential structure of the temporal evolution of the cognitive activity;

wherein the method further comprises classifying the at least one signal into at least one subcategory of cognitive activities by means of the characterisation module; and wherein the classification of the signal is performed by means of the machine learning algorithm previously trained with training signals which are classified into at least one predefined subcategory of cognitive activity, and wherein the result label is fed back into the machine learning algorithm to improve precision thereof.

* * * * *